United States Patent [19]

Coelho et al.

[11] Patent Number: 5,557,943
[45] Date of Patent: Sep. 24, 1996

[54] RAPID COOLING THROUGH A THIN FLEXIBLE MEMBRANE

[75] Inventors: Philip H. Coelho; Terry Wolf, both of Rancho Cordova, Calif.

[73] Assignee: ThermoGenesis Corporation, Rancho Cordova, Calif.

[21] Appl. No.: 986,525

[22] Filed: Dec. 7, 1992

Related U.S. Application Data

[62] Division of Ser. No. 495,765, Mar. 19, 1990, Pat. No. 5,168,712.

[51] Int. Cl.$^6$ ................................. H25D 17/02
[52] U.S. Cl. .................... 62/376; 62/64; 62/373
[58] Field of Search .................. 62/62, 63, 64, 62/373, 375, 376

[56] References Cited

U.S. PATENT DOCUMENTS

| | | | |
|---|---|---|---|
| 2,061,427 | 11/1936 | King | 62/437 X |
| 2,274,284 | 2/1942 | Vore | 62/64 X |
| 2,286,514 | 6/1942 | Stebbins | 62/63 |
| 2,914,445 | 11/1959 | Clarke | 62/373 |
| 3,007,319 | 11/1961 | Ogden | 62/376 X |
| 3,027,734 | 4/1962 | Mills | 62/64 X |
| 3,049,890 | 8/1962 | Ruppel | 62/376 X |
| 3,090,134 | 5/1963 | Morrison | 62/63 X |
| 3,096,627 | 7/1963 | Morrison | 62/64 X |
| 3,154,084 | 10/1964 | McKee | 62/376 X |
| 3,320,757 | 5/1967 | Pauliukonis | 62/376 |
| 3,406,531 | 10/1968 | Swenson et al. | 62/375 X |
| 3,440,831 | 4/1969 | Thompson | 62/64 X |
| 3,753,357 | 8/1973 | Schwartz | 62/64 |
| 3,774,524 | 11/1973 | Howard | 62/64 X |
| 3,875,754 | 4/1975 | Faust et al. | 62/64 X |
| 3,888,092 | 6/1975 | Fisher | 62/376 |
| 3,952,536 | 4/1976 | Faust et al. | 62/373 |
| 3,995,444 | 12/1976 | Clark et al. | 62/376 X |
| 4,245,483 | 1/1981 | Murai | 62/376 |
| 4,251,995 | 2/1981 | Pert et al. | 62/64 X |
| 4,530,816 | 7/1985 | Douglas-Hamilton | 62/64 X |
| 4,565,073 | 1/1986 | Lavender | 62/373 |
| 4,630,448 | 12/1986 | Bilstad et al. | 62/64 X |
| 4,637,226 | 1/1987 | Sitte | 62/64 X |
| 4,654,217 | 3/1987 | Nagoshi | 62/64 X |
| 4,657,768 | 4/1987 | Nagoshi | 62/64 X |
| 4,689,963 | 9/1987 | Sakai | 62/64 |
| 4,715,195 | 12/1987 | Kucza | 62/378 X |
| 4,745,354 | 5/1988 | Fraser | 62/375 X |
| 4,840,034 | 6/1989 | Liberman | 62/64 |
| 4,840,035 | 6/1989 | Liberman | 62/64 |

FOREIGN PATENT DOCUMENTS 0137147  10/1979  Japan ............................. 62/373

OTHER PUBLICATIONS

Hulland, E. L., "Immersion Freezing of Poultry", Jan. 1958, pp. 60–61 of Refrigerating and Meat Packing Conference.
Fisher, Alan R., National Frosted Foods, Inc. "The Flexible Froster" #222, Aug. 1939 Quick Frozen Foods.

*Primary Examiner*—Christopher Kilner
*Attorney, Agent, or Firm*—Bernhard Kreten

[57] ABSTRACT

Rapid cooling or freezing of foodstuffs, perishables or blood products is accomplished by using a thin film membrane to totally envelope the foodstuffs or blood product only during the heat extraction period. This thin film encapsulation system closes around the item and is held tightly to the item by atmospheric and/or hydrostatic pressure. Once the item is encapsulated, low temperature heat transfer fluids are then circulated on the exterior surface of the membrane, thus extracting the heat within the item through the thickness of the membrane. Upon completion of the necessary chilling or freezing, the atmospheric and/or hydrostatic pressure is withdrawn and the chilled or frozen item is extracted.

7 Claims, 10 Drawing Sheets

RAPID COOLING THROUGH A THIN FLEXIBLE MEMBRANE

This application is a division of application Ser. No. 07/495,765, filed Mar. 19, 1990, U.S. Pat. No. 5,168,712.

FIELD OF THE INVENTION

The present invention relates to the art of rapid cooling or freezing of articles such as foodstuffs, perishables or blood products using low temperature liquids and to prevent the contamination of the foodstuffs, perishables or blood products by migration of toxins to these articles in the heat transfer fluid.

BACKGROUND OF THE INVENTION

The need for rapid heat extraction from foodstuffs, human tissues and fluids is well documented.

Direct-contact, heat transfer liquids such as liquid nitrogen and liquid carbon dioxide are well known and are used in extremely low temperature applications such as cryogenic freezing. Such freezing requires expensive equipment to maintain the liquid state of the coolant by the proper combination of pressure and low temperature to prevent evaporation and consequent loss of vaporized heat transfer liquid to atmosphere. Since there is a direct relationship between frozen food that tastes fresh and the rate at which the food is frozen, some of the more expensive foods are cryogenically frozen with liquid nitrogen, etc. despite its high freezing costs. However, for the economical freezing of less sensitive foodstuffs, the extreme low temperatures of liquid nitrogen and liquid carbon dioxide and attendant expense of the specialized equipment to handle it are not deemed cost effective.

Another trend in the food industry is discernable. That is, institutional food preparation is now frequently prepared at least partially at a remote location ("hub" kitchen) and then transported to the site of ultimate consumption, for example at a public school. As a result, the "hub" kitchen must first properly prepare the food by at least partially cooking, and then quickly reduce the food temperature below 40° F. to minimize the development of any bacteria, such as salmonella, which would adversely effect the ultimate consumer. For example, a pan having a 2 inch depth within which food has been cooked is subject to a known prior art refrigeration device whose manufacturers claim a drop in temperature from 180° F. to 40° F. in approximately 90 minutes. While in some instances this may be possible, certain dense foods will still have a core temperature in excess of 40° well after the manufacturer's suggested allotted time in these commercial freezers, providing an unacceptable bacterial risk.

Some institutional kitchens will accelerate the chilling process by removing the lid which covers the cooked food. This allows heat and vapor to leave the tray in order to accelerate the chilling process. Clearly, vapor loss ultimately will dehydrate the food, at least along an outer periphery, and subsequent freezing provides the phenomenon known as "freezer burn". More importantly, the open cooking trays serve as an incubator for airborne bacteria which increases the likelihood of communal contamination which exacerbates the problem.

Similarly, blood plasma contains proteins which are labile and decay at all temperatures above −30° C. This decay is occurring at the highest rate in the temperatures above fusion (about −2° C.). Consequently, the faster the plasma can be frozen, the greater the quantity of these proteins that will remain in the plasma for therapeutic purposes. The importance of rapid freezing of blood plasma can be best illustrated by noting that the most labile protein, the clotting Factor VIII, is often reduced in content by 50% during the elapsed time between collection from the donor and being frozen to −30° C. Nevertheless, the Factor VIII concentrate which finally survives the manufacturing process has a retail market of 600 million USD annually.

Most conventional prior art food and blood products freezers comprise refrigeration units in which the heat transfer medium is air—a gas. Although it is well known that liquids are more efficient than gases as heat transfer fluids, when freezing or chilling foodstuffs or blood products, direct contact with the heat transfer fluid is acceptable only if the fluid is substantially non-toxic and/or has tolerable levels of migration of toxins to food, and/or does not lend an acceptable taste or texture to the foodstuffs.

Because of their intrinsically low toxicity, as well as their low boiling points, minimal density and high volatility, the normal refrigerating gases such as $LN_2$, $CO_2$ or mechanically refrigerated air will pass no toxin on to the items to be chilled or frozen.

Pure water, the most obvious, inexpensive and excellent heat transfer fluid is unusable as a means of freezing foodstuffs or blood products because water freezes at 0° C. (32° F.) and most blood products and foodstuffs freeze between −1° C. and −4° C. (31° F. and 24° F.). Since the rate of heat transfer is proportional to the temperature difference between the heat transfer liquid (which is cold) and the warmer foodstuffs or blood products, only liquids which remain low in viscosity (i.e. pumpable) down to at least −20° C. to −30° C. (4° F. to −22° F.) can rapidly freeze foodstuffs or blood products which freeze at approximately −2° C. to −4° C. (30°–24° F.).

Recognizing the intrinsic heat absorbing superiority of liquids over gases, refrigeration specialist have attempted to reduce the freezing point of water by adding salts or glycols to water. For example a 50/50 mix of glycol and water has a freezing point of −30° C. (−22° F.) and a 25/75 mix of calcium chloride and water has a freezing point of −29° C. (−21° F.) thus allowing them the ability to rapidly freeze foodstuffs or blood products. However, the addition of these freezing point lowering chemicals to water has some serious drawbacks.

Both calcium chloride and propylene glycol have levels of toxicity that are cause for concern. In fact in the food industry, any foodstuffs coming into contact with water containing any percentage mix of glycol or chloride must be protected by a water proof, FDA approved plastic cover. In the blood products industry, where health concerns are even more acute, no such mixtures are currently in use.

A further problem with such heat transfer mixtures is that they become viscous at low temperatures and thus cling to the surface of a packages foodstuff and are carried out of the freezing bath on the surface of the packaging. This surface contamination is both messy and toxic and consequently must be washed off with pure water before continuing on for further handling. Since by definition this washing must be done by water warmer than 0° C., this cleansing process adds heat to the frozen product, which is not desired, and creates a new waste fluid which must be disposed of in an environmentally suitable manner.

A further problem is that when food items are introduced to a chamber which the chloride or glycol mixture resides, it is virtually impossible to stop certain amounts of moist, outside air from invading the chamber. Once inside, the moisture in the air condenses out and goes into solution with the chloride or glycol mixture, thereby continually altering the percent water in the mixture. Since the freezing point rises with the increasing percentage of water, continual monitoring and adjustment of the mixture must be maintained.

Chlorofluorocarbon refrigerants such as the Freon (trademark of the DuPont Company) compositions have previously been employed in closed loop non-direct contact refrigeration systems in which the circulating refrigerant is never permitted to come into direct contact with the articles to be chilled. Toxins present in refrigerants of this type have, with two exceptions noted below, prevented these refrigerants and/or solvents from being approved by regulatory authorities such as the United States Food and Drug Administration (FDA) for direct contact with foodstuffs.

To date it is believed that only two chlorofluorocarbons, CFC 12, (dichlorodifluoromethane) and the proprietary mixture of applicant's called Instacoolant™ containing CFC-113, have ever been approved by the FDA for direct contact with human food. The CFC-12 composition is, however, only marginally suitable for use in immersion or spray contact freezing of foodstuffs because of its relatively low boiling point (−30° C.) which results in the high loss of CFC-12 to the atmosphere despite expensive recovery systems and the consequent expense of regular replacement of lost fluid. A suitable direct contact heat transfer liquid must therefore also have a suitably high boiling point above normal ambient temperatures, preferably above 50° C., in order to maintain tolerable losses due to evaporation.

The following patents reflect the state of the art of which applicant is aware, in so far as these patents appear germane to the instant process, particularly as dictated by the claims. It is respectfully submitted that these patents neither teach singly nor render obvious when considered in any conceivable combination the claimed nexus of the applicant's invention. Moreover, these patents are included to discharge the applicant's acknowledged duty to divulge known prior art.

| INVENTOR | PATENT NO. | ISSUE DATE |
| --- | --- | --- |
| H. G. Vore | 2,274,284 | Feb. 24, 1942 |
| H. Y Stebbins | 2,286,514 | June 16, 1942 |
| F. H Clarke | 2,914,445 | Nov. 24, 1959 |
| C. A Mills | 3,027,734 | April 3, 1962 |
| W. L. Morrison | 3,090,134 | May 21, 1963 |
| W. L. Morrison | 3,096,627 | July 9, 1963 |
| S. S. Thompson | 3,440,831 | April 29, 1969 |
| Schwartz | 3,753,357 | Aug. 21, 1973 |
| Howard | 3,774,524 | Nov. 27, 1973 |
| Faust, et al. | 3,875,754 | April 8, 1975 |
| Pert, et al. | 4,251,995 | Feb. 24, 1981 |
| Douglas-Hamilton | 4,530,816 | July 23, 1985 |
| Bilstad, et al. | 4,630,448 | Dec. 23, 1986 |
| Sakai | 4,689,963 | Sept. 1, 1987 |

Each of these patents can generally be characterized with respect to one type of infirmity or another discussed generally, supra. For example, many of the systems included to show the state of the art are brine or glycol type systems. Thus they may cause solutions to adhere to the chilled article. One brine system, Stebbins uses a pliant conveyor with an optional vacuum. Sealing problems may attend this structure. Another infirmity with respect to some of the prior art is that they have the expense associated with liquid nitrogen or carbon dioxide systems. All systems that utilize clorflurocarbons (CFC) suffer from the malady that the CFCs are susceptible to vaporization and escape into the atmosphere. Another infirmity is that some of the prior art involving plastic covering and medical products do not contemplate any form of heat extraction.

SUMMARY OF THE INVENTION

The instant invention is distinguished over the known prior art in a plurality of ways. At its broadest, the instant invention contemplates a membrane which is interposed between the article to be chilled or frozen and the chilling freezing liquid. Upon placement of the article in contact with the chilling liquid, the membrane interposed therebetween precludes the through passage of the cooling liquid therebeyond. This means that vaporization into the atmosphere has been minimized as well as the leaching of the freezing liquid onto or into the article being chilled will have reached negligible levels.

Viewed from another broad aspect, a membrane is described which is able to withstand extremely cold temperatures without losing its ability to conform to the external contour of the product being chilled. The significance of this phenomena is that the membrane, when placed in contact with the article, will conform to the contour of the article without any air gaps. By placement of the chilling liquid on the other side of the membrane remote from the article, the most efficient means for thermal transfer will be manifested thereby.

Viewed from another broad perspective, circulation of the chilling liquid is viewed as one feature which distinguishes the instant invention from the known prior art, particularly when considering the foregoing summary features. By providing a strong liquid current against the membrane and therefore the article being chilled, the greatest temperature differential exists between the article and a fresh supply of cooling liquid at all times, providing and encouraging the most rapid heat transfer possible. Stated alternatively, the circulation of liquid enhances heat loss through convection as well as conduction.

Viewed from another aspect, the instant invention broadly encompasses an efficient method of chilling articles in which the flexible membrane is encouraged to conform to the exterior periphery of the article to be chilled in the presence of either hydrostatic pressure and/or a vacuum which draws the membrane close to the article. This assures that air gaps (a source of inefficiency in heat transfers) will have been kept to a minimum.

The heat transfer fluid in U.S. Pat. No. 4,803,842, and U.S. Pat. No. 4,730,460 is an excellent choice for use with foodstuffs and blood products as evidenced by the permission granted by the FDA to use this fluid for the freezing of foodstuffs (in Oct. 1989) and blood products (March 1987). However, the liquid formulation contains CFC-113, which like CFC-12 is a member of a family of chlorinated fluorocarbons which, when emitted into the atmosphere, are suspected of reducing the earth's ozone layer. Consequently one of the purposes of this invention is to utilize the superior heat transfer properties and low migration through plastics described in U.S. Pat. Nos. 4,803,842 and 4,730,460 while reducing the emissions into the atmosphere essentially to zero.

Further this invention may be used to take advantage of excellent heat transfer properties of water/glycol or water chloride without significant migration of their toxins to the foodstuffs or blood products and without the invasion of the moist outside air which complicates the practical usage of such mixtures as a liquid freezant.

The use of water/glycol or water/chloride is within the scope of this invention because the membrane separates these liquid freezants from the actual removable articles being cooled.

Succinctly stated, a cooling apparatus and method is disclosed in which the apparatus includes a control panel, a housing supporting the control panel, and a heat exchange area for cooling liquid contained within a cavity associated with the housing. The cavity is configured to receive be batches either a tray, a series of trays or a series of pouches which are supported on a framework. In some instances, a lid is associated with the batch structure to facilitate in the cooling process.

OBJECT OF THE INVENTION

Accordingly, it is a primary object of the present invention to provide a novel and useful apparatus and method for cooling articles.

A further object of the present invention is to provide a device and method as characterized above which is extremely safe to use and minimizes the risk of volatile components associated with the cooling liquid from leaching or permeating either the article being cooled or the atmosphere.

A further object of the present invention is to provide a device and method as characterized above in which the temperature drop of the article to be chilled occurs precipitously so that bacteria which thrives within the temperature range between 40° and 180° F. are less likely to incubate.

A further object of the present invention is to provide a device as characterized above wherein the cooling occurs with requisite efficiency that there is no need to expose the articles being cooled to air thereby minimizing vapor loss of the articles being cooled or exposing the article to airborne contaminants.

It is an object of the present invention to provide a device as characterized above which is extremely durable in construction, safe to use and lends itself to mass production techniques.

Viewed from one vantage point, it is an object of the present invention to provide a device as characterized above wherein a device has been provided for rapidly cooling perishables which includes liquid refrigerant disposed in a container and provided with a heat exchange structure for maintaining the refrigerant in a cold, heat absorbing state. A portal on the container allows perishables access to the liquid refrigerant and a membrane is interposed between the portal and the perishables which prevents the escape of liquid refrigerant beyond the container. The membrane is configured in such a way that perishables can be immersed into a cavity associated with the container for intimate contact with the refrigerant and the membrane substantially envelopes the perishables leaving no air gaps so that rapid cooling is provided.

Viewed from a second vantage point, it is an object of the present invention to provide a barrier which is interposed between a perishable to be cooled and refrigerant which includes a flexible membrane provided with sufficient pliability to conform to an external contour of the perishable which is to be refrigerated. The membrane is selected from a family of membranes having sufficient non-porosity to prevent the migration of the refrigerant therebeyond so that the perishable article being refrigerated while being enveloped by the barrier cools quite rapidly and the refrigerant does not migrate therebeyond.

Viewed from yet a third vantage point, it is an object of the present invention to provide a method for refrigerating a perishable in which the steps include providing a liquid refrigerant in a container, chilling the refrigerant to maintain a temperature lower than the perishable, introducing the perishable into the container such that the perishable loses heat to the liquid but no refrigerant can migrate beyond the container, encapsulating the perishable, causing the refrigerant to conform to the perishable, and thereafter releasing the perishable so that the perishable has been quickly and efficiently cooled because of good thermal transfer.

These and other objects will be made manifest when considering the following detailed specification when taken in conjunction with the appended drawing figures.

BRIEF DESCRIPTION OF THE DRAWING FIGURES

BRIEF DESCRIPTION OF PREFERRED EMBODIMENTS

Figure 1:
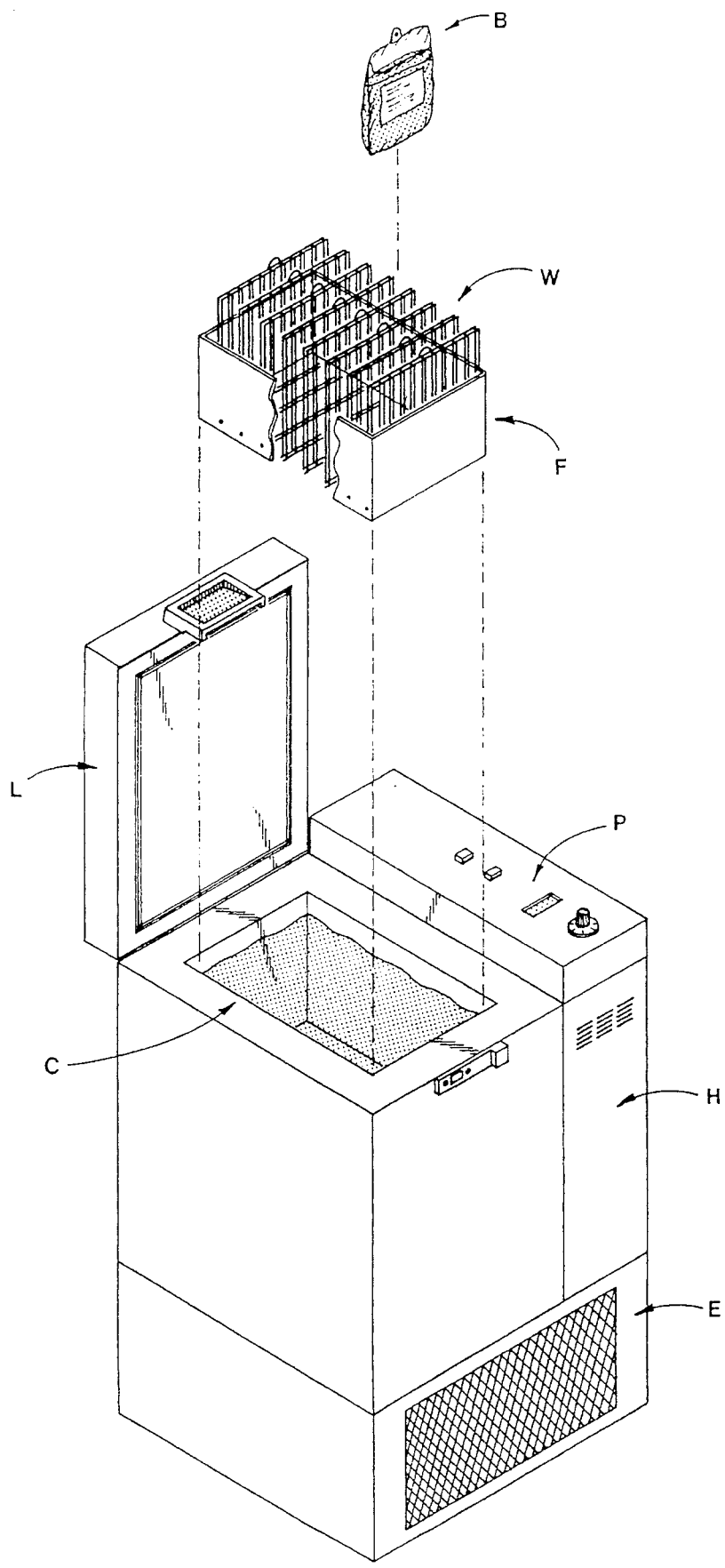
FIG. 1 is a perspective, exploded parts view of prior art.
Figure 2:
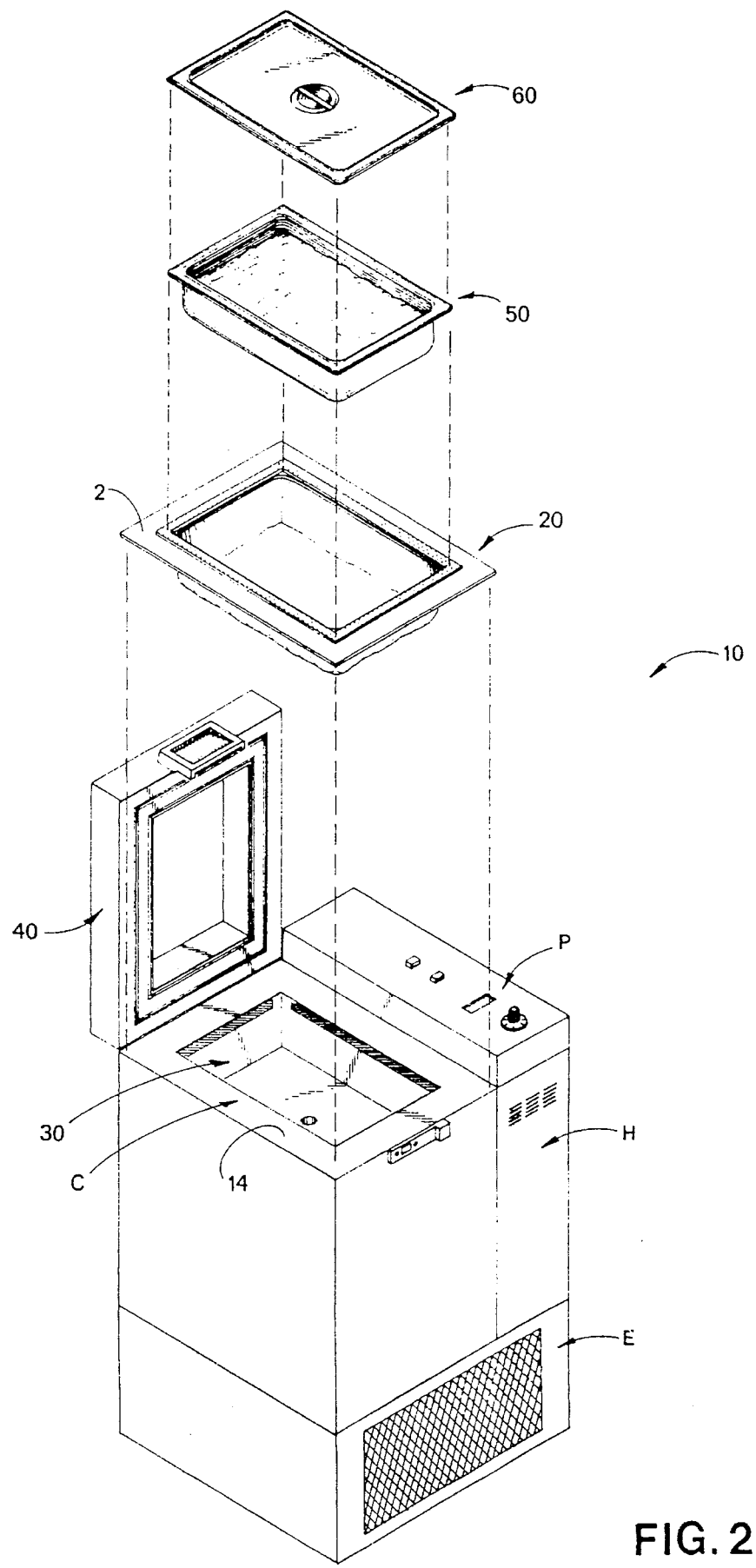
FIG. 2 is an exploded parts perspective of the apparatus according to the present invention in one form.

Referring to the drawings now, wherein like reference numerals refer to like parts throughout the various drawing figures, reference numeral 10 is directed to the apparatus according to the present invention in its first embodiment, as exemplified in FIGS. 2 through 5; reference numeral 100 is directed to the embodiment according to the second version of FIGS. 6 through 9; and reference numeral 110 is directed to the version shown in FIGS. 10 through 13, the third embodiment according to the present invention.

Perspective can be attained by considering the known prior art of FIG. 1, which exemplifies applicants' known existing commercial unit. There a housing H is shown of substantially rectangular configuration having a control panel P on one side thereof, and a heat exchange area E for providing heat transfer for coolant which is selectively admitted into a cavity C. A lid L cooperates with occluding the cavity C so that articles disposed within the cavity can be chilled without additional exposure to ambient air conditions. As shown, the current commercial version includes a wire assembly W held together by a frame F within which a plurality of bags B containing blood plasma are nested for immersion into the cavity and coolant to provide rapid chilling. As mentioned supra, this structure and associated coolant have been approved by the FDA for direct contact with the bags B which store blood plasma. The heat transfer fluid associated with the Figure 1 apparatus is more completely described in U.S. Pat. 4,803,842. All halogenated hydrocarbons such as CFC's, HCFC's, HFC's and mixtures thereof are useful in the system described hereinafter because of the reliable separation between ambient conditions and refrigerant.

Major aspects of the instant invention benefit from and utilize structure shown in FIG. 1. Accordingly, those features share like symbols.

In essence, however, each embodiment of the instant invention shares the following common attributes. All provide a flexible membrane which occludes the cavity C so that cooling liquid contained therewithin can only contact articles to be chilled or frozen by first contacting the flexible membrane. In this manner, CFCs cannot volatilize and enter into the atmosphere because the membrane provides a barrier. Should the cooling liquid be a water/glycol mix or a chloride/water mix, then placement of an article to be cooled on one side of the membrane while having the cooling liquid on the other side of the membrane solves the longstanding prior art problems of having the chilling liquid contact and adhere to the outer surface of the article being chilled and having the outside air invade and combine with the refrigerated mixture.

More particularly, and with reference to FIGS. 2 through 5, those salient differences which distinguish the instant invention over the prior art of FIG. 1 will now be explored. As shown, the membrane 20 is supported by a flange 2 which extends around the periphery of the cavity C and rests on a shelf 14 circumscribing the outer periphery of the cavity 30. Please see FIG. 5. The cavity itself includes a series of vertically depending side walls 32 and a bottom wall 34 which provides an open top container so that refrigerant 24 can pass therethrough in a manner to be defined.

Figure 4:
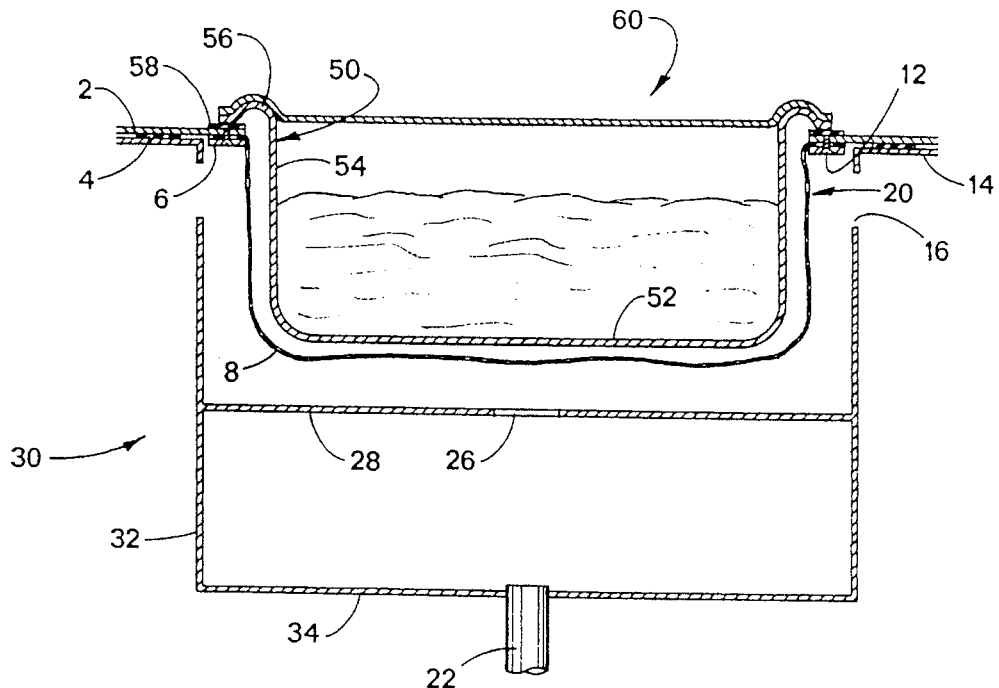
FIG. 4 is a sectional view schematic detailing certain structure associated with utilization of the apparatus shown in FIGS. 2 and 3.

In essence, the shelf 14 shown in FIG. 4 supports the flange 2 indirectly, through a seal 4 extending around the periphery of the shelf and flange's areas of interconnection. The seal 4 minimizes the likelihood of vapor from escaping from the refrigerant area and precludes the admission of contaminants within the refrigerant.

The flange 2 supports the flexible poly etherurethane film 8 forming part of the flexible membrane structure 20 in depending relation by attachment of the membrane via a bead 6 underlying the flange 2 and fastened thereto by means of a fastener 12.

The flexible membrane, while preferably formed from polyether film can also be formed from other material, such as polycarbonate, teflon, silicone, or polyester polyurethane, although the polyether film has been found to have superior characteristics. In essence, the film is characterized as having the ability to conform to or envelope an article which is to be chilled only during the chilling process. Thereafter the membrane releases the article when further chilling is not needed. As such, the membrane has the ability to remain flexible at extremely low temperatures. This allows it the ability to conform closely to the exterior contour of the article being chilled. In addition, the film has the ability of barely resisting that transfer, so that it efficiently transmits temperature differences that exist on opposite sides of its boundary.

FIG. 4 shows the placement of a tray 50 on a top surface of flange 2 so that a portion of the tray 50 extends within the cavity 30 but protected by the flexible membrane structure 20 from contact with the refrigerant as shall be explained. The tray 50 has an open topped configuration with a bottom wall 52 and a side wall 54 which extends around the outer periphery of the bottom wall, thereby defining an open topped receptacle, and a rim 56 which extends laterally outward from a top portion of the side walls 54. The rim has an arcuate crossection, as shown in FIG. 4. It is adapted to rest upon a gasket 58 carried on a top surface of the flange 2 which renders less likely that CFCs will migrate therebeyond.

A top 60 has a periphery 62 complemental to the rim 56 of tray 50 to close the tray 50 thereby minimizing the likelihood that desired steam associated with cooking will be lost. This avoids needless dehydration of the food and reduces the likelihood that airborne impurities and bacterium will enter into the food, had this tray been left open.

Figure 3:
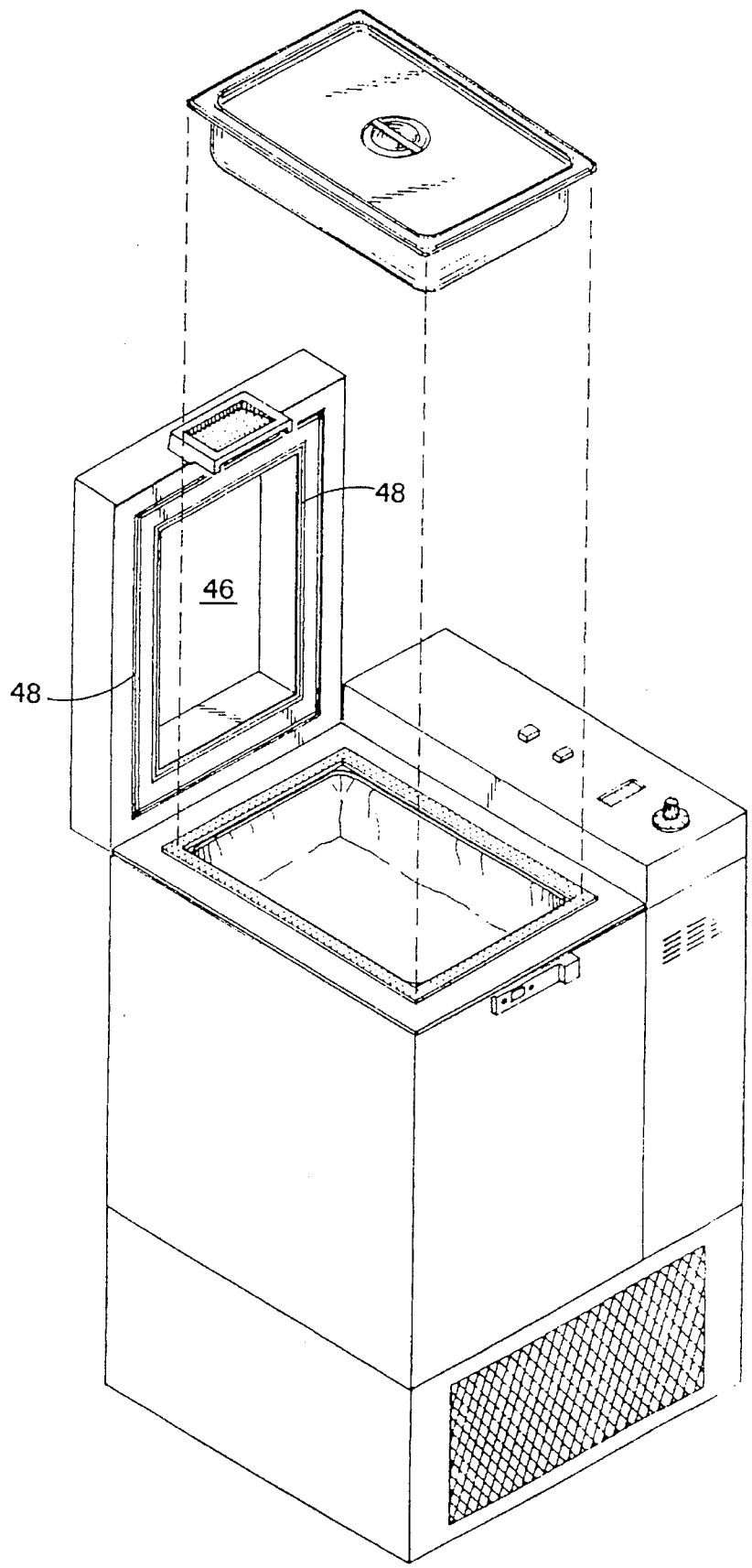
FIG. 3 is a perspective view similar to FIG. 2 showing various components of FIG. 2 in a partially assembled configuration.
Figure 5:
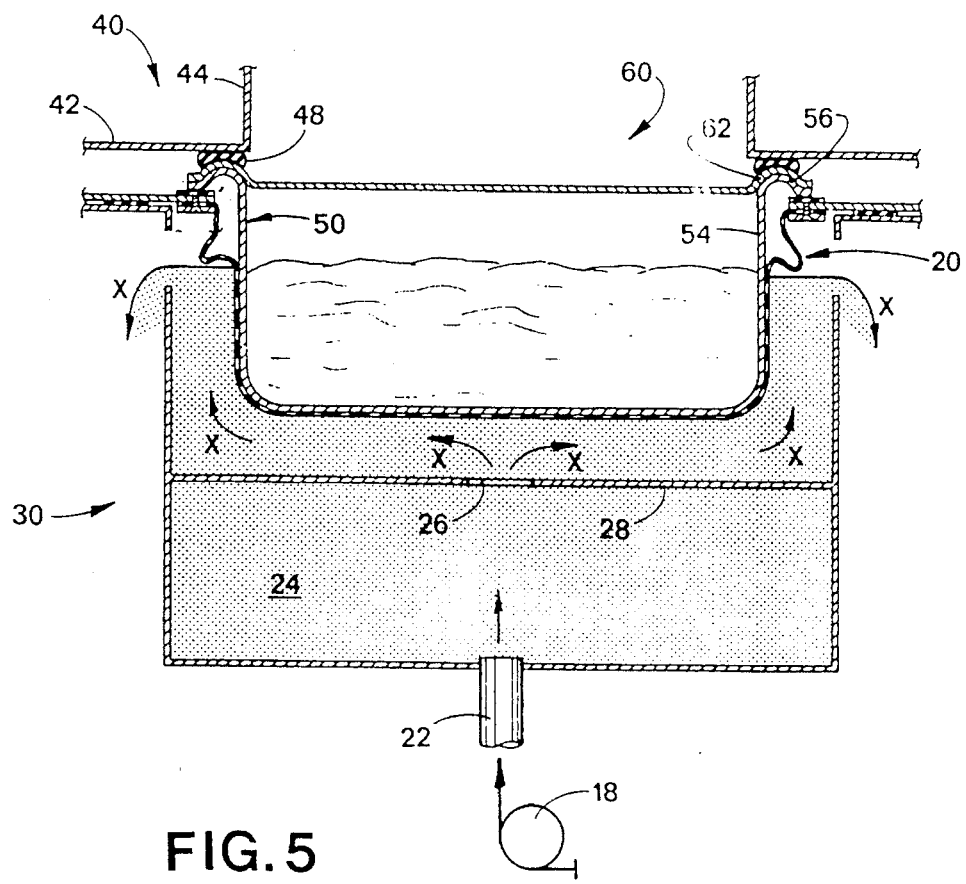
FIG. 5 is a view similar to FIG. 4 showing the cooling operation actually in progress.

With respect to FIG. 3 and 5, certain detail of the lid 40 can now be explored. As shown, the lid 40 includes a circumscribing horizontal wall 42 which generally overlies the flange 2 previously discussed. The horizontal wall 42 communicates with a vertical wall 44 which extends upwardly substantially conforming to the contour of the side walls 54 of the tray 50. Thus, in conjunction with a further wall 46 of the lid parallel to the bottom wall 52, a well has been defined which overlies the tray 50. Note the presence of first and second weatherstripping type sealing means or gaskets 48 circumscribing the area defined by the well. A first inner weatherstrip 48 is adapted to register with the undulation defining both the rim 56 of the tray and the periphery 62 of the top. A second, concentric outer weatherstrip 48 is adapted to register with a top surface of the flange 2 should the inner weather strip 48 not be needed. In this manner, a reliable seal has been provided between the lid and the remaining structure to preclude the through passage of CFCs.

Appreciation of the operation of the present invention should now be evident when consideration the exemplary showings of FIGS. 4 and 5. More particularly, a pump 18 delivers the refrigerant through a conduit 22 into the cavity 30 defined by the side walls 32 circumscribing the bottom wall 34. Refrigerant 24 is admitted therewithin. A plurality of drain holes 16 circumscribe portions of the side walls 32 to allow the refrigerant to spill off and be recirculated so that a maximum temperature gradient is provided where the flexible membrane 20 contacts the refrigerant 24. It is preferred that a high flow rate is provided of the refrigerant, to provide maximum temperature differential. As shown, refrigerant flows along the direction of the arrows X and spills over the drain 16 so that the height at which the refrigerant will rise is limited by the placement of these drains 16. Optionally, the current pattern can be altered by the placement of a baffle 28 within the cavity 30. As shown, at least one hole 26 is centrally disposed within the baffle 28 to provide the current shown by the arrows X. Of course other types of circulatory patterns could be effected.

As shown in FIG. 5, the membrane 20 has the ability to respond to hydrostatic pressure exerted by the refrigerant 24 in its upward travel from the pump 18, through the conduit 22 and past the drain 16. Because the flexible poly etherurethane film 8 remains pliant during the entire operation and conforms to the outer periphery of the tray 50, there are no air gaps. Assuming that the food is disposed within the tray as shown in the FIG. 4 and FIG. 5 drawings, rapid cooling is afforded by the process just described. It is the ability of the flexible poly etherurethane film 8 to conform to the outer periphery of the article to be chilled and its low resistance to heat transfer that provides one of the benefits according to the present invention. The film 8 also releases the tray 50 when the refrigerant recedes.

Attention is now directed to FIGS. 6 through 9 which reflects an alternative embodiment for affording the same type of beneficial, rapid cooling. Those areas of divergence between the previously discussed embodiment and this one will now be focused on, with the similarities to be assumed.

More particularly, the second embodiment 100 features a pouch type of system for bringing about rapid chilling. In essence, the pouch structure 120 includes a substantially planar horizontal surface 122 which is adapted to rest on shelf 14 which underlies the lid L and surrounds the cavity C. A single weatherstripping 48 circumscribes the lid L for sealing purposes. Similarly, a gasket 126 (FIG. 9) underlies the horizontal surface 122 for the attendant sealing purpose.

Figure 6:
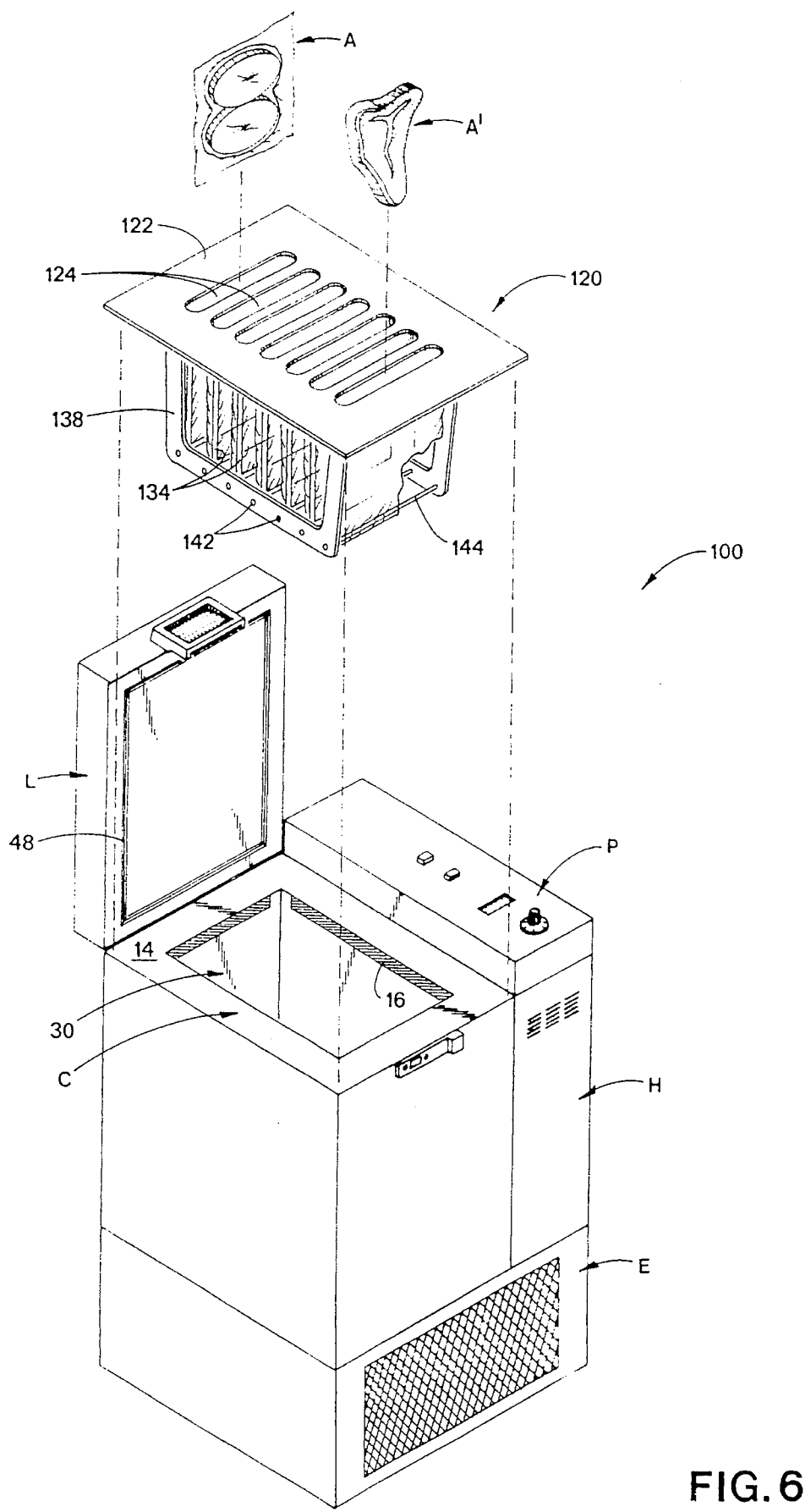
FIG. 6 is an exploded perspective view, similar to FIG. 2 showing a variant according to the present invention.
Figure 7:
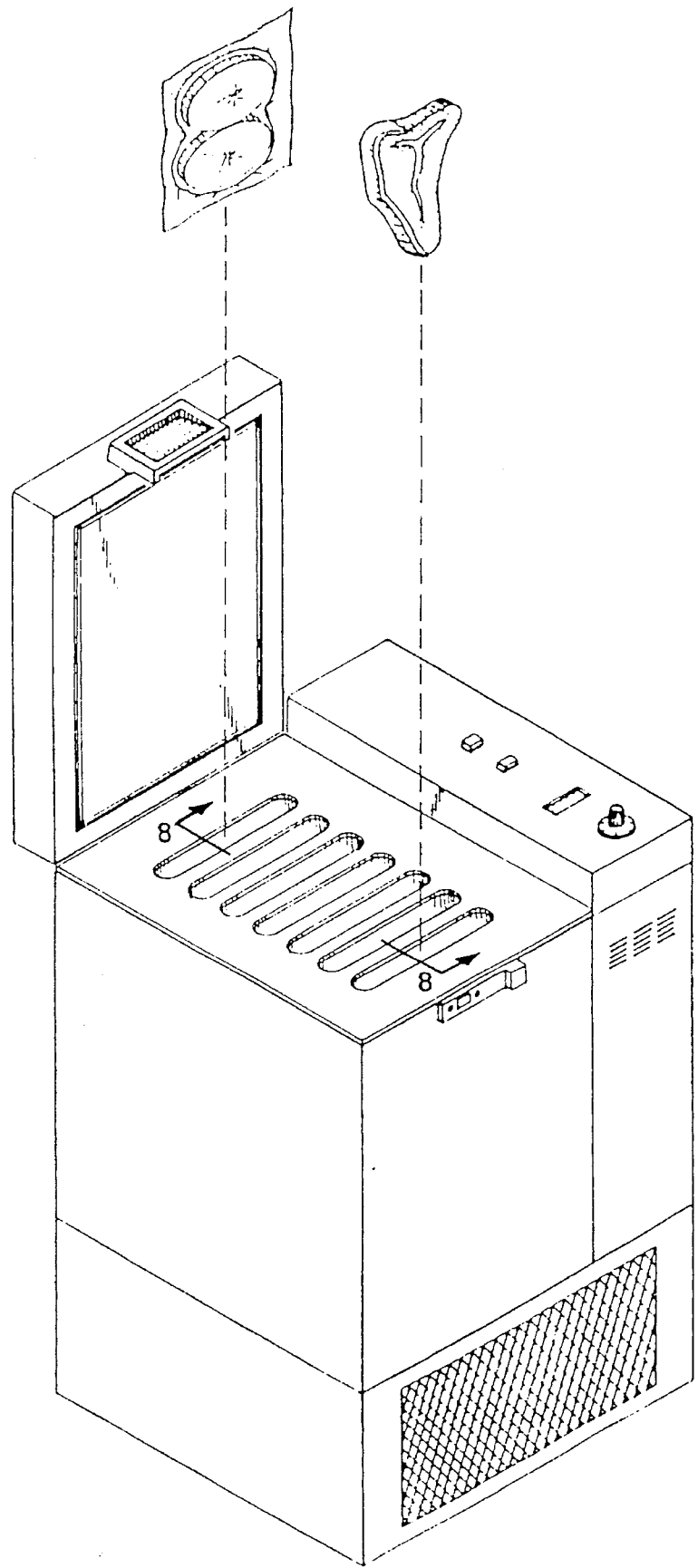
FIG. 7 is a perspective view showing the second embodiment in a deployed, ready to use configuration.

As shown in FIGS. 6 through 9, a plurality of slots 124 are adapted to pass through the horizontal surface 122. These slots will allow articles to be chilled to pass therethrough. As shown in FIG. 6 for example, an article A and A' are dimensioned with respect to the slots and vise versa to allow them to be slidably disposed within the slot 124.

Figure 8:
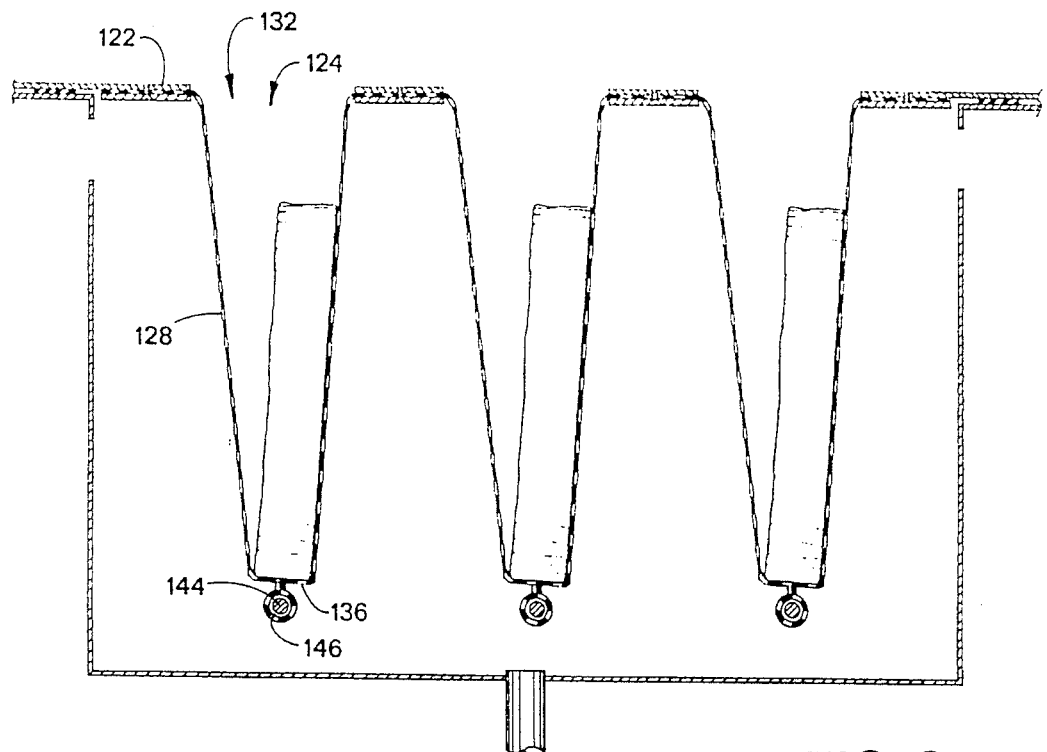
FIG. 8 is a sectional view taken along lines 8—8 of FIG. 7 showing the apparatus immediately prior to engaging the cooling process.
Figure 9:
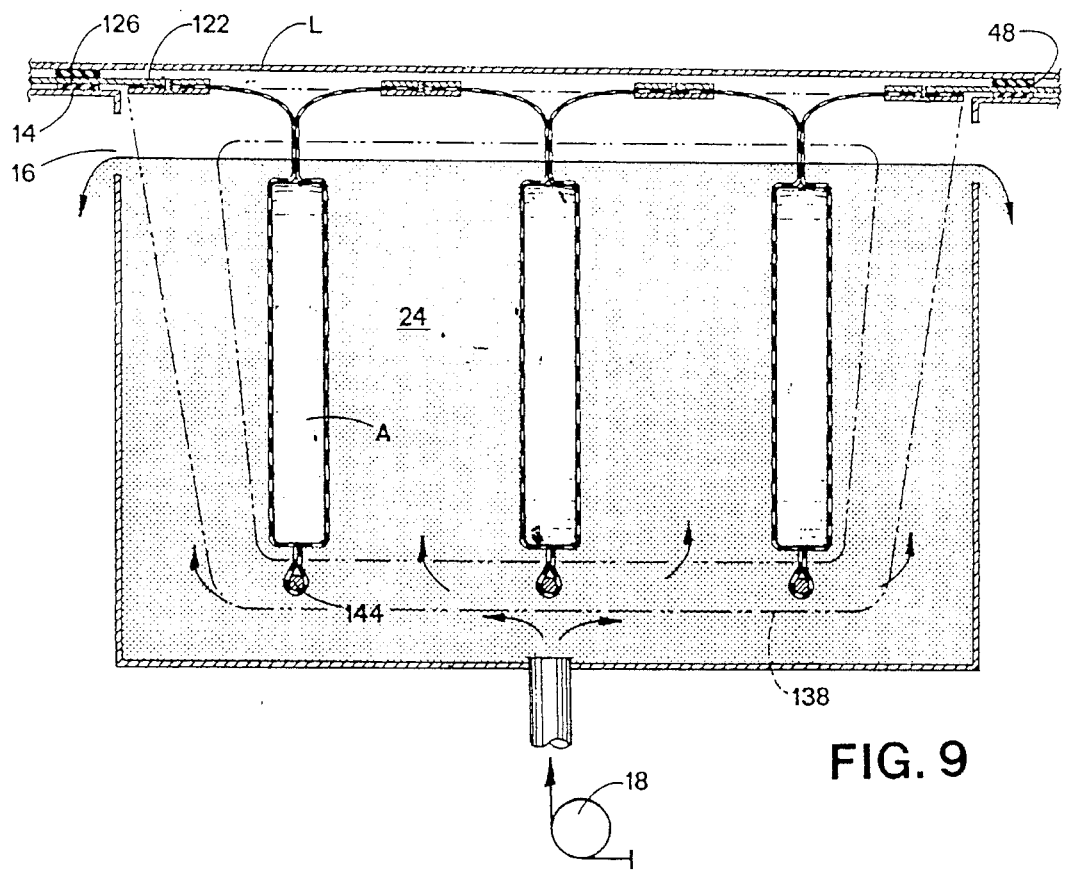
FIG. 9 shows the cooling process in operation, when contrasted with that which is shown in FIG. 8.

Each slot communicates with a pouch shaped membrane formed from flexible poly etherurethane film 128. Thus, a plurality of pouches has been provided, each with its own opening 132 and seam structure so that side walls 134 and a bottom wall 136 are impervious to the refrigerant 24. As shown in FIGS. 8 and 9, the vertical rise and presence of refrigerant 24 causes hydrostatic pressure which forces the plural pouches defined by the flexible film 128 to close, forcing out the air vertically and then occluding the opening 132 and the slots 124 so that no air gaps are provided between the membrane and the refrigerant, affording rapid chilling. Stated alternatively, the presence of the refrigerant 24 encapsulates the perishable article A. The membrane conforms to the exterior periphery defined by the perishable article while the refrigerant comes in contact with only the membrane. Thereafter, the absence of refrigerant 24 causes the perishable article to be released and removed from the pouches which extend down from the horizontal surface 122.

It should be noted that there is a tendency for these depending pouches to migrate away from the oncoming refrigerant 24 as the refrigerant level rises in the cavity 30. Accordingly, a framework 138 is provided which precludes migration of the pouches so that they are retained in substantially vertically arrays. As shown in FIG. 6, a framework 138 having a substantially upwardly extending open U shaped configuration depends from a bottom wall of horizontal surface 122. The frame 138 is provided in pairs, on opposed distal extremities of each slot 124 so that each pouch is bracketed at least at its lower most extremity near the bottom wall 136 by the frame 138.

These spaced parallel frames 138 include a lower bight portion and upwardly extending legs. The bight portion of the frame 138 includes apertures 142 through which rods 144 are adapted to pass. The rods are threaded through opening 146 contained in the bags so that the pouches are held substantially in vertical configuration to prevent wandering when the refrigerant is placed in tangential registry therewith.

Figure 13:
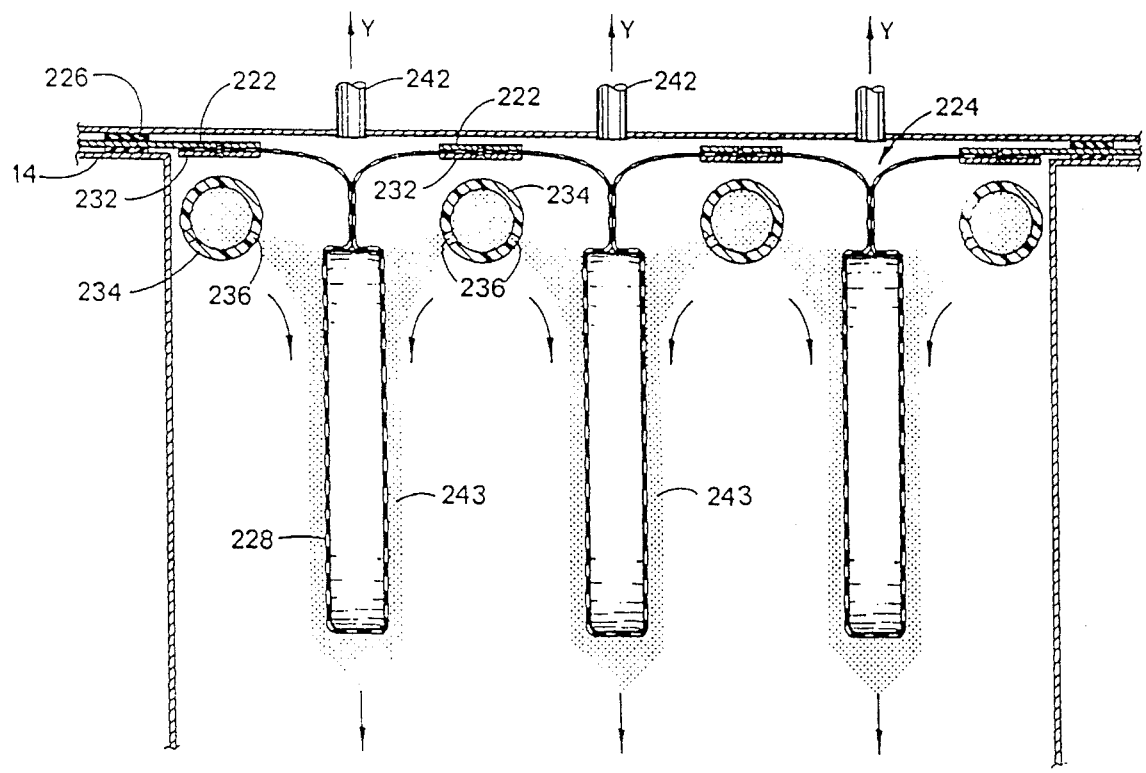
FIG. 13 is similar to FIG. 12 showing the refrigerant in its deployed condition.

Attention is now directed to FIGS. 10 through 13 which reflect a third embodiment. As shown, the pouch structure membrane 220 which includes the horizontal cover plate surface 222 merely has the pouches 228 depending from its slots 224 freely and without use of the support bracket as was the case in the previous embodiment. As shown in FIG. 13, the horizontal surface 222 seals the pouch structure 220 to shelf 14 by means of gasket 226. Pouches 228 collectively form a membrane 229 which is clamped to the bottom surface of planar horizontal surface 222 at slot openings 224 by clamping pieces 232. The pouches 228 go from an open configuration of FIG. 12 to a closed configuration of FIG. 13 in the following manner.

Figure 10:
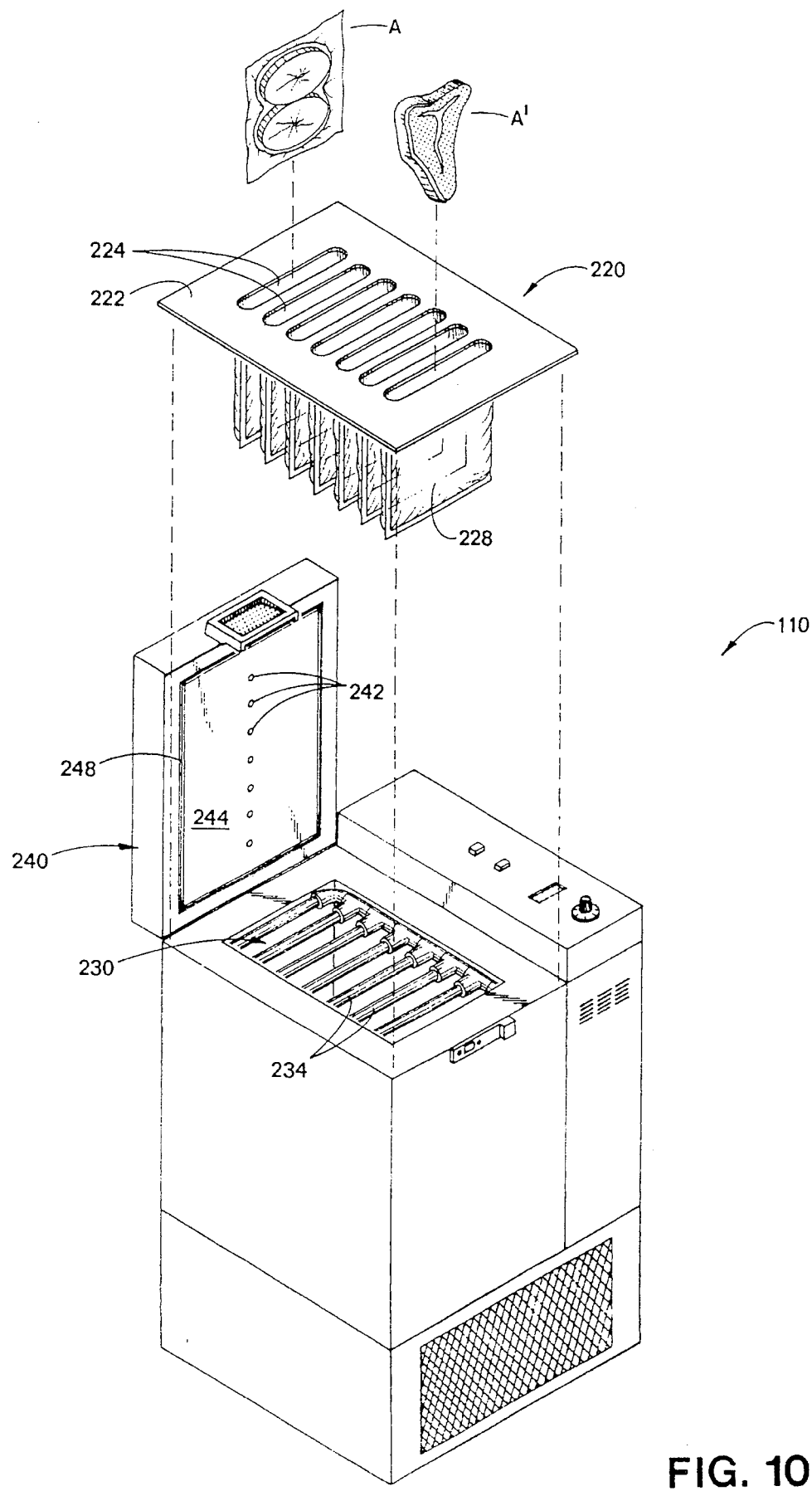
FIG. 10 is a perspective view, similar to FIG. 6, showing a third form of the invention.
Figure 11:
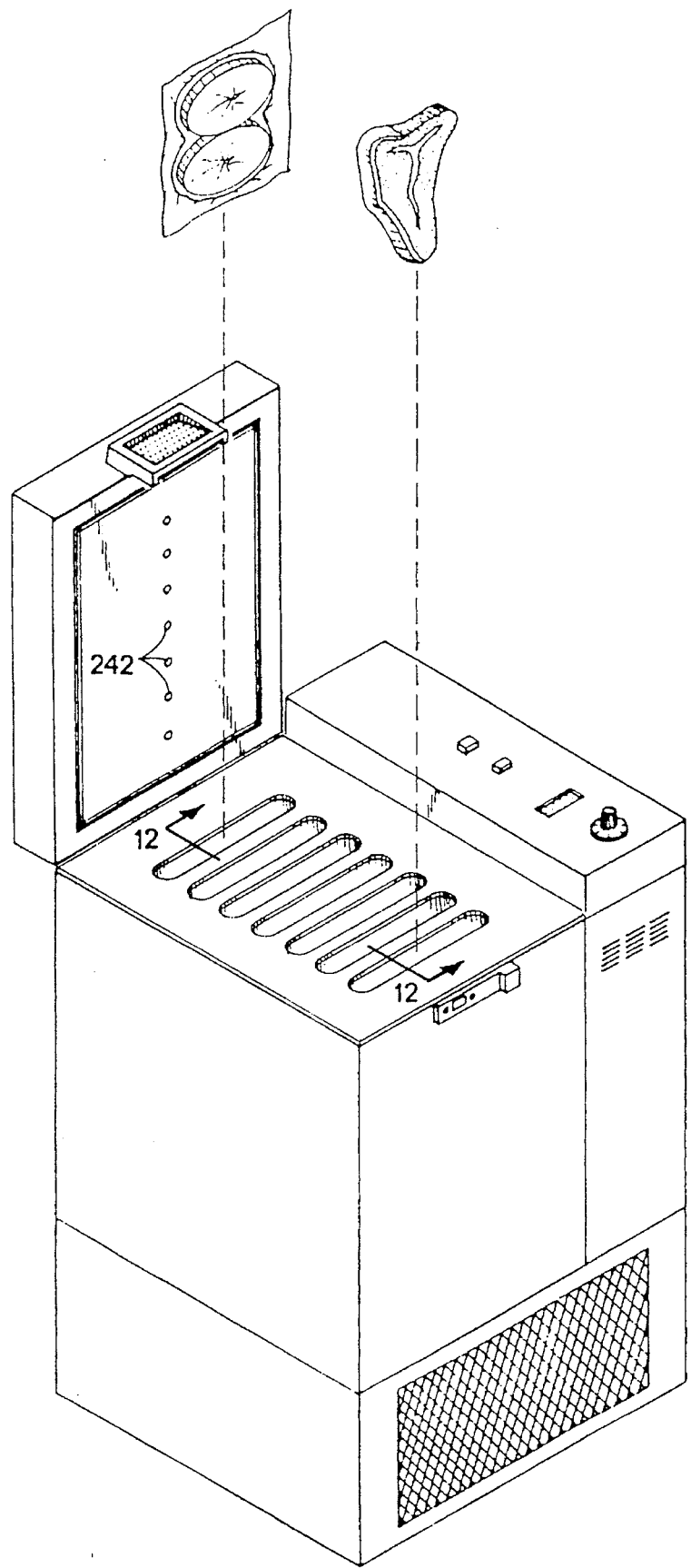
FIG. 11 is a view similar to FIG. 10, showing partial assembly of the apparatus according to the present invention.
Figure 12:
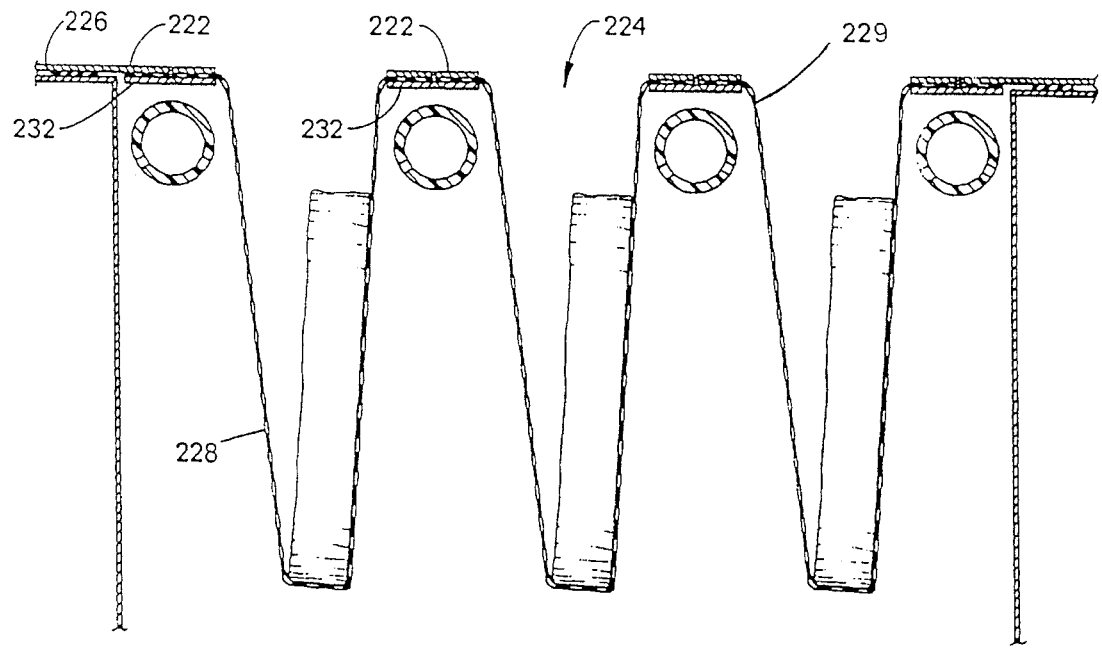
FIG. 12 is a sectional view taking along lines 12—12 of FIG. 11.

As shown in FIG. 10, the cavity 230 has a plurality of transversely disposed tubes 234 which carry the refrigerant therewithin. These tubes 234 are provided with apertures 236 which cause the refrigerant to spray therebeyond. The apertures 236 are oriented so that the refrigerant 243 coalesces and impinges upon the pouches 228 as shown in FIG. 13. The pouches 228 are caused to embrace the article A or A1 by means of a modified lid 240 as shown in FIG. 10. More particularly, the lid is provided with the depicted weather stripping 248 and also includes a series of passageways 242 on the surface 244 of the lid which is adapted to overlie the pouch structure 220.

Preferably, one passageway 242 is oriented to overlie one opening defined by slot 224 so that all slots 224 have a passageway 242 as shown. Each passageway 242 communicates with a source of negative pressure to provide a vacuum such that pneumatic pressure is provided within the pouches 228. This evacuates the pouches 228 by withdrawing air contained therewithin along the direction of the arrow Y in FIG. 13. Thus, a vacuum is the source of causing the pouch to conform to the article to be chilled while the refrigerant is being sprayed on the outer surface of the pouch 228 to provide the efficient cooling. In this version, the pump 18 of the earlier versions does not fill the cavity as described previously, but rather feeds the tubes 234.

In use and operation, the article to be cooled is placed within the cavity and the lid is placed thereon. Energization of the machine causes the refrigerant to contact the article in such a manner that the membrane coalesces around the article to be refrigerated. In all cases, although the pouch structure is capable of being removed for cleaning, the refrigerant is not exposed to ambient conditions with the same type of frequency or severity as is the case in the known prior art. As a result, volatilization or vaporization of the refrigerant does not occur at least to the same magnitude as is known in the prior art. Where the refrigerant is not a CFC but is a brine solution, glycol solution, or other heat transfer liquid, the membrane provides a barrier precluding contact with the article to be cooled.

Moreover, having thus described the invention, it should be apparent that numerous structural modifications and adaptations are resorted to without departing from the scope and fair meaning of the instant invention as defined by the claims hereinafter and as articulated in the foregoing.

We claim:

1. A device for fast freezing perishables, comprising, in combination:

a container having an open top;

a liquid refrigerant disposed in said container which is provided with means for maintaining the refrigerant at a temperature to enable the fast freezing of the perishables;

a removable cover plate having top and bottom surfaces and a plurality of slotted openings;

said cover plate being hermetically secured to said container top;

each said slotted opening having a pouch formed of thin-walled flexible plastic material with the pouch opening hermetically sealed to the bottom perimetric edge of said slotted opening to depend therefrom into the container interior;

a plurality of tubular spray heads mounted in said container below said cover plate to direct liquid refrigerant against said pouches;

an insulated closure member moveable from an open position exposing said slots for inserting perishables into said pouches to a closed position hermetically sealing said closure to said cover plate top surface; and vacuum means acting between said cover plate top surface and said insulated closure to collapse said pouches around said perishables whereby fast freezing is achieved by said liquid refrigerant spray aided by improved heat transfer resulting from the vacuum created close contact between the pouches and perishables.

2. The device of claim 1 wherein the pouches are formed of a continuous folded membrane with membrane portions extending from the pouch openings being clamped to the underside of the cover plate at locations bordering the slots.

3. The device of claim 2 wherein the membrane is formed of a polyetherurethane film.

4. The device of claim 2 wherein the vacuum means comprises a plurality of tubes extending through the closure member and connected to a common source of vacuum, the vacuum inlet of each tube being spaced above a respective slot.

5. A device for fast freezing perishables, comprising, in combination:

a container having an open top;

a liquid refrigerant disposed in said container which is provided with means for maintaining the refrigerant at a temperature to enable the fast freezing of perishables;

a removable cover plate having top and bottom surfaces and a plurality of slotted openings;

each slotted opening having a pouch formed of thin-walled flexible plastic material with the pouch opening hermetically sealed to the bottom perimetric edge of said slotted opening to depend therefrom into the container interior;

a plurality of spray heads mounted in said container to direct liquid refrigerant against said pouches; and an insulated closure member moveable from an open position exposing said slotted openings for inserting perishables into said pouches to a closed position sealing said closure to said cover plate top surface.

6. The device of claim 5 wherein the pouches are formed of a continuous folded membrane with membrane portions extending from the pouch openings being secured to the cover plate at locations bordering the cover plate openings.

7. The device of claim 6 wherein the openings comprise a plurality of parallel, spaced slots and wherein said spray heads comprise tubular spray heads with each pouch being positioned between a pair of spray heads.

* * * * *